(12) United States Patent
Schenk et al.

(10) Patent No.: US 11,073,519 B2
(45) Date of Patent: Jul. 27, 2021

(54) LATERAL FLOW TESTING

(71) Applicant: Global Life Sciences Solutions Germany GmbH, Dassel (DE)

(72) Inventors: Alexander Schenk, Dassel (DE); Klaus Hochleitner, Dassel (DE); Suzana Kiel, Gottingen (DE); Marcel Thieme, Dassel (DE); Wei Sun, Dassel (DE)

(73) Assignee: Global Life Sciences Solutions Germany GmbH, Dassel (DE)

( * ) Notice: Subject to any disclaimer, the term of this patent is extended or adjusted under 35 U.S.C. 154(b) by 0 days.

(21) Appl. No.: 15/300,558

(22) PCT Filed: Mar. 17, 2015

(86) PCT No.: PCT/EP2015/055579
§ 371 (c)(1),
(2) Date: Sep. 29, 2016

(87) PCT Pub. No.: WO2015/150067
PCT Pub. Date: Oct. 8, 2015

(65) Prior Publication Data
US 2017/0115287 A1      Apr. 27, 2017

(30) Foreign Application Priority Data
Mar. 31, 2014   (GB) ................................. 1405770

(51) Int. Cl.
*G01N 33/558* (2006.01)
*G01N 33/52* (2006.01)

(52) U.S. Cl.
CPC ......... *G01N 33/558* (2013.01); *G01N 33/525* (2013.01)

(58) Field of Classification Search
CPC ........................... G01N 33/558; G01N 33/525
(Continued)

(56) References Cited

U.S. PATENT DOCUMENTS 5,712,170 A    1/1998  Kouvonen et al.
5,998,220 A   12/1999  Chandler
(Continued)

FOREIGN PATENT DOCUMENTS

CN    1570642 A      1/2005
EP     127147 A1     1/2003
(Continued)

OTHER PUBLICATIONS

Sajid et al., "Designs, formats and applications of lateral flow assay; A literature review", Journal of Saudi Chemical Society, Sep. 1, 2014, 17 pages.
(Continued)

*Primary Examiner* — Sally A Merkling
(74) *Attorney, Agent, or Firm* — Eversheds Sutherland (US) LLP

(57) ABSTRACT

In a lateral flow test (LFT) device, the liquid conduit element 20 is formed from a substrate 21, 22 or 24 having at least two layers, including a first layer 21b, 22b or 24b not exceeding 75 μm in thickness formed from a porous material for wicking liquid, and a second layer 21a, 22a or 24a of additional thickness formed from a generally non-porous polymer material acting as backing layer. The layered arrangement is incorporated into an LFT device to reduce sample volume requirements.

17 Claims, 4 Drawing Sheets

(58) Field of Classification Search
USPC .......................................................... 422/421
See application file for complete search history.

(56) References Cited

U.S. PATENT DOCUMENTS

| | | | |
|---|---|---|---|
| 6,979,576 B1* | 12/2005 | Cheng | G01N 33/558 |
| | | | 435/283.1 |
| 7,632,687 B2 | 12/2009 | Gokhan | |
| 7,704,702 B2 | 4/2010 | Keren et al. | |
| 7,972,670 B2* | 7/2011 | Seitz | B32B 7/10 |
| | | | 428/40.1 |
| 7,998,753 B2 | 8/2011 | Chiku et al. | |
| 8,586,375 B2 | 11/2013 | Chan | |
| 2003/0211636 A1* | 11/2003 | Bedian | C07K 16/44 |
| | | | 436/518 |
| 2004/0022678 A1* | 2/2004 | Komagoe | G01N 33/525 |
| | | | 422/400 |
| 2011/0045578 A1* | 2/2011 | Kawamata | G01N 33/558 |
| | | | 435/287.1 |
| 2015/0192575 A1* | 7/2015 | Van Amerongen | ............... |
| | | | G01N 33/54386 |
| | | | 422/69 |

FOREIGN PATENT DOCUMENTS

| | | | |
|---|---|---|---|
| EP | 1271147 | * | 1/2003 |
| EP | 2273269 A1 | | 1/2011 |
| JP | 2011-179955 A | | 9/2011 |
| JP | 4918627 B2 | | 4/2012 |
| JP | 2012-251789 A | | 12/2012 |
| JP | 2013-079913 A | | 5/2013 |
| WO | 92/01226 A1 | | 1/1992 |
| WO | 2006/080438 A1 | | 6/2008 |
| WO | 2014/025251 A1 | | 2/2014 |

OTHER PUBLICATIONS

International Search Report and Written Opinion regarding International Application No. PCT/EP2015/055579, dated Jun. 16, 2015, 12 pages.
Search Report regarding GB Application No. 1405770.7, dated Oct. 3, 2014, 3 pages.
Chinese Office Action for CN Application No. 201580028583.1 dated Nov. 23, 2017 (15 pages).
Japanese Office Action for JP Application No. 2016-559395 dated Feb. 26, 2019 (5 pages).

* cited by examiner

LATERAL FLOW TESTING

CROSS-REFERENCE TO RELATED APPLICATIONS

This application is a filing under 35 U.S.C. 371 of international application number PCT/EP2015/055579, filed Mar. 17, 2015, which claims priority to GB application number 1405770.7, filed Mar. 31, 2014, the entire disclosures of each of which are hereby incorporated by reference.

FIELD OF THE INVENTION

The present invention relates to lateral flow test (LFT) devices also known as lateral flow assays or lateral flow immunochromatographic assays, and components thereof in particular the construction of liquid conduit elements within such devices.

BACKGROUND OF THE INVENTION

LFT devices are intended to detect the presence or absence of a target analyte in a liquid sample.

Conventionally, a series of liquid conduits, for example capillary pads, such as pieces of porous paper or sintered polymer are formed on a support. A known arrangement employs various liquid conduit elements, including a first sample liquid receiving element which acts as a sponge and holds an excess of sample liquid. Once soaked, the fluid propagates to a second element, known as a conjugate release pad, in which the manufacturer has stored the so-called conjugate, typically a dried format of bio-active particles in a dissolvable matrix that includes reagents to produce a chemical reaction between the target molecule and its chemical partner that has been immobilized on the particle's surface. As the sample dissolves the particles a reaction takes place to bind the analyte to the particle. Typically, a second colour-changing reagent located at a specific distance along the conjugate pad, or on a third element, and is used to capture particles on which are bound the analyte to provide a test result. A third colour-changing reagent further along the liquid path than the second reagent is often used to capture all particles, and so is used as a control to ensure that the liquid sample has propagated past the second reagent. After passing the reaction zones of the second and third reagents the liquid sample enters the final porous wick material element, acting as a waste container.

Many millions of these devices are produced worldwide annually for home use. Typically, these tests are used for medical diagnostics in the home, in a clinic or in a laboratory. Home testing kits are becoming more popular, for example home pregnancy tests. Since the urine used as a sample for that test is plentiful, then there is no need to worry about the amount of liquid needed to implement the assay. However, not all samples are so abundant. For example, other assays could be more readily available for home testing of blood but any more than a few drops of home-produced blood is conventionally difficult to obtain at home without help or the addition of buffer liquids, so such devices are not generally used as home tests. If a very low volume of sample were sufficient, then home blood testing would be more likely. Also a hurdle for development of some tests is the cost of the reagents employed. Equally if a lower sample volume were employed, then less reagent should be needed and costs would be reduced in many instances. LFTs are not restricted to clinical or diagnostic tests. Non clinical applications include testing food and water for contaminants as well as bio-threat agents and other environmental contaminants. In these tests too, the amount of sample available can be very small, or the reagents used can be expensive.

The inventors have devised a way to reduce sample and reagent volume in an LFT, without substantially compromising the effectiveness of the device.

The invention is defined by the claims. In an embodiment, the invention provides a liquid conduit element for a lateral flow test device, the element being formed from a substrate having at least two layers, including a first layer not exceeding 75 µm in thickness formed from a liquid porous material, and a second layer of additional thickness formed from a generally non-porous polymer material.

The use of such a first porous layer is advantageous because less sample containing liquid is needed, and the additional polymer layer adds strength for handling during manufacture of the LFT device, as well as allowing flexibility in construction of the elements.

In an embodiment, the first layer is 30 to 70 µm in thickness, and preferably 40 to 60 µm in thickness and more preferably about 50 µm in thickness.

In an embodiment the first layer is a cellulose acetate (CA) membrane, or a regenerated cellulose (RC) membrane formed by treatment of a CA membrane, for example, in order to eliminate the acetate residues from the cellulose structure.

In an embodiment, the first layer has an average pore size of 0.5 to 3 µm, and for CA preferably about 1.2 µm, and for RC preferably about 1.0 µm.

In further embodiments, the first layer is formed from nitrocellulose optionally having grafted thereto polyethylene glycol (PEG).

In an embodiment, the second layer is transparent and is formed from a plastics material for example a polyester, such as polyethylene terephthalate (PET).

In an embodiment, the polymer layer is about 100 µm in thickness.

The invention provides also a lateral flow test (LFT) device as defined by the claims, optionally including a liquid conduit element according to the first aspect.

In an embodiment, the liquid conduit element includes at least a sample receiving element, and a reaction element in turn including one or more reagents for reacting with an analyte or further reagents bound to said analyte, and at least the sample receiving element is formed from the layered substrate material mentioned above.

In an embodiment the LFT device further includes a conjugate storage element formed from the layered substrate material mentioned above.

In an alternative, the sample receiving element includes a portion which provides conjugate storage.

In an embodiment the reaction element is formed from a further layered material including a first layer formed from nitrocellulose membrane and a second layer formed from PET.

In an embodiment, the first reaction element layer is about 40 to 60 µm in thickness thick, and the second layer is about 100 µm in thickness.

In an embodiment the first reaction element includes an uncovered portion for allowing liquid evaporation.

The invention extends to any inventive combination of features described herein, whether or not that combination is mentioned explicitly herein.

BRIEF DESCRIPTION OF THE DRAWINGS

The invention can be put into effect in numerous ways, illustrative embodiments of which are described below with reference to the drawings, wherein.

DETAILED DESCRIPTION OF THE INVENTION

The lateral flow test (LFT) or lateral flow immunochromatographic assay, introduced in 1988 by diagnostic test manufacturers, is the most common commercially available point-of-care (POC) diagnostic device. Today, POC LFT devices for pregnancy (detecting hCG levels) and ovulation confirmation, screening for infectious diseases and drugs of abuse, and for measurement of protein markers in blood to aid rapid clinical diagnostics of life-threatening events such as heart attack, stroke, and deep-vein thrombosis are manufactured in very large numbers: >$10^7$/year for pregnancy alone. Tests are also available nowadays for home testing; these are non-prescription tests that can be obtained at the pharmacy or through the Internet, however there is still an enormous potential untapped.

Figure 1:
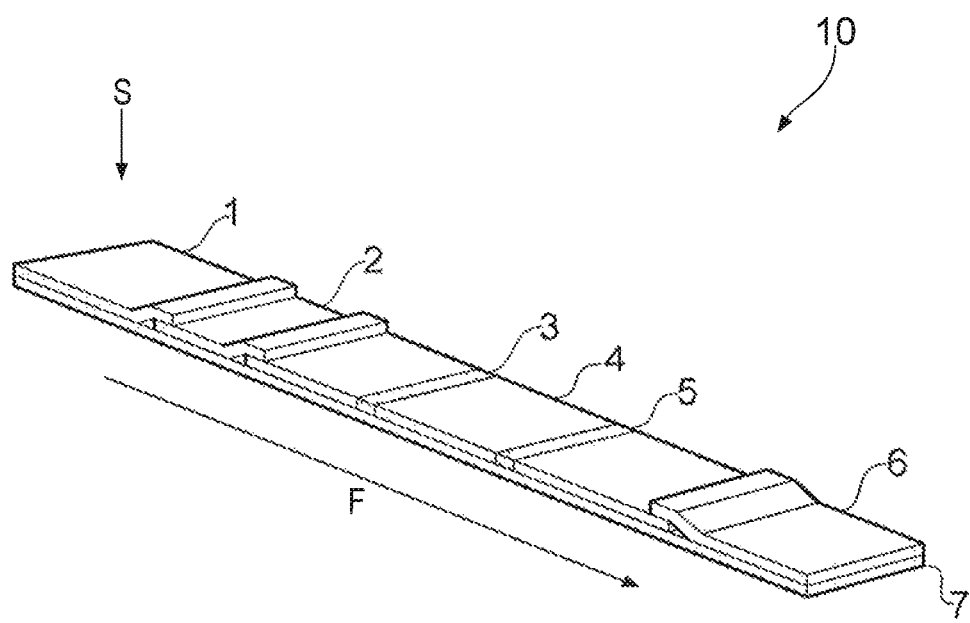
FIG. 1 shows a schematic view of a known liquid conduit of a LFT device.

An immunoassay needs several functionalities which are typically realized with a string of different liquid conduit elements as shown in FIG. 1. Usually such known devices comprise substrates in the form of: a cotton linter sample receiving pad 1 typically 320 μm in thickness; a glass fibre conjugate release pad 2 typically 350 μm in thickness on which dissolvable conjugates are stored; a nitrocellulose reaction membrane 4 typically 100 μm in thickness; a test line 3; a control line 5; a cotton linter end wick 6; and a backing 7. The typical functioning of the LFT is as described above. In some cases, a cover tape (not shown) is also used on the assay strip to prevent fast solvent evaporation and hold the elements in place.

Typically, the receiving pad 1 and release pad 2 consist of cellulosic papers, glass fibre pads, or so called non-woven (e.g. polyester) pads that both have low binding capacities for biomolecules, i.e. they readily give up any biomolecules sorbed thereon, for example so that less than 3 μg/cm$^2$ can be sorbed onto the material. Whereas the reaction membrane on which the test results are displayed consists of a material with a high binding capacity for biomolecules, i.e. molecules sorbed onto the nitrocellouse are held by the material with high affinity, for example such that of at least 3 μg/cm$^2$ of proteins can be sorbed onto the material.

The receiving pad 1 is routinely coated with reagents that adjust the specific parameters of the sample liquid that is added to the test system with respect to defined parameters as e.g. pH, ion strength and supplementary chemicals as e.g. surfactants.

Additionally, the receiving pad may perform additional functions as e.g. but no limited to retaining red blood cells if whole blood is used as a sample whereas the liquid part of the blood is allowed to flow along the liquid conduit elements through the test system.

The main disadvantage with these known LFT devices is the overall volume of sample needed to complete the assay. In other words, the elements of the LFT need to be filled with sample at least up to the control line 5, and so minimum sample volumes in excess of 50 μl are the norm. Given that a finger prick yields about 25-300 of blood, but only 10-15 μl of liquid phase (plasma), it is apparent that conventional LFT devices are deficient.

Figure 2:
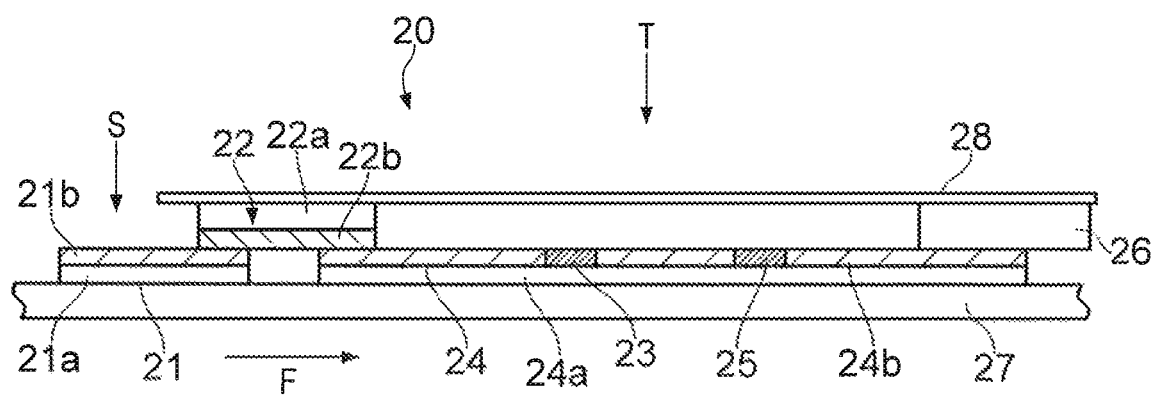
FIG. 2 shows a schematic view liquid conduit for an LFT device.

FIG. 2 shows an example of an arrangement of liquid conduits 20 for an LFT device which arrangement reduces the amount of liquid sample required compared to known LFT devices. Whilst the general arrangement of elements is similar to those described above in relation to FIG. 1 and whilst the functional steps are similar, the construction in FIG. 2 is improved for low liquid volume requirement. In this embodiment substrates forming liquid conduit elements of the device are mounted to an adhesive layer of a backing material 27. A sample S is applied to a sample receiving pad 21 which is formed from two layers—a 100 μm thick transparent PET backing layer 21a, and a cellulose acetate membrane 21b having a membrane thickness of around 50 μm, and oriented such that the membrane is uppermost. In contact with the membrane of the receiving pad 21 is a conjugate pad 22 formed from the same layered material as the receiving pad 21, but also storing a conjugate reagent. The conjugate pad 22 is oriented such that its membrane layer 22b contacts the membrane 21b of the receiving pad 21, thereby allowing a capillary action for sample liquid to travel in the direction of arrow F, from the receiving pad 21 and on to the conjugate pad 22. Liquid from the sample S propagates through the conjugate pad 22 and on to the reaction pad 24, which in this case is formed from another two layer material—a nitrocellulose membrane layer 24b having a thickness of 50 μm and a backing layer 24a of 100 μm thick PET. This pad includes test line reagents 23 and 25 in this case colloidal gold, to capture analytes bound to the conjugate reagents employed and capture of unbound conjugate reagents respectively. The arrangement further includes a conventional cotton linter 26 to absorb any excess liquid. A conventional cover tape 28 is used also. Test results are visible in the direction of arrow T.

Figure 3:
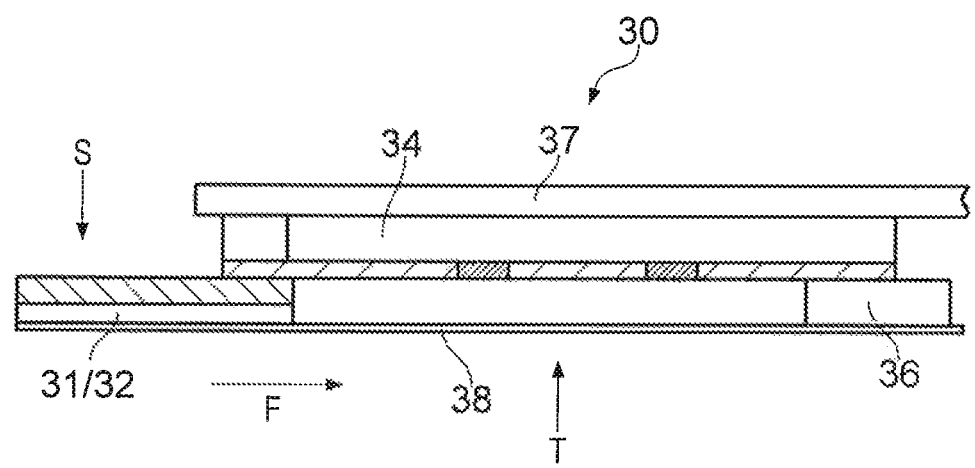
FIG. 3 shows a schematic view of a further liquid conduit for an LFT device.

FIG. 3 shows another example of an arrangement of liquid conduits 30 for an LFT device which reduces the amount of liquid sample required compared to known LFT devices, with functionality similar to the examples described above. In this embodiment substrates forming the liquid conduit elements of the device are again mounted to an adhesive layer of a backing material 37. A combined sample receiving pad and conjugate storage pad 31/32 is provided formed from the same material as the pad 21 described above. This combined pad is in contact with a reaction pad 34 of the same material as the pad 24. The respective membranes of the pads 31/32 and 34 are in contact to provide a capillary path for the liquid sample S, again to propagate in the direction of arrow F. A waste pad 36 is provided, and the elements are covered by a cover tape 38. Test results are visible in the direction of arrow T. This embodiment simplifies the construction shown in FIG. 2.

Figure 4:
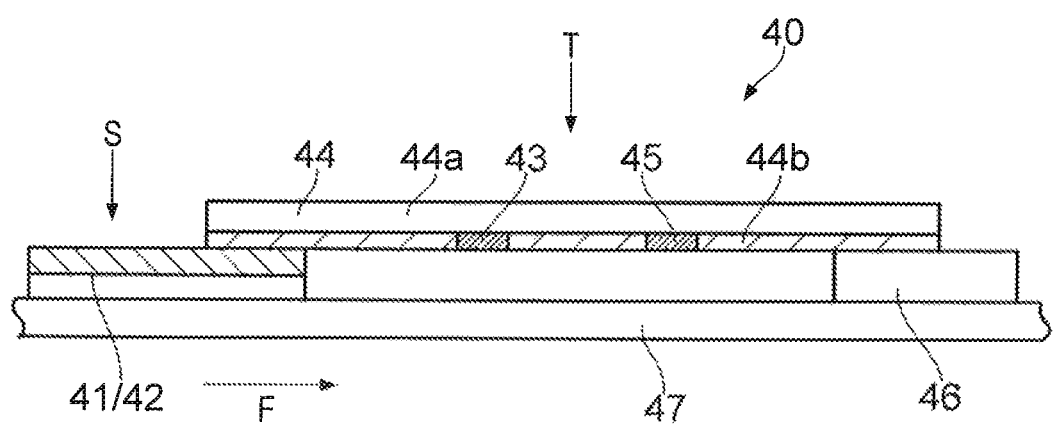
FIG. 4 shows a schematic view of a further liquid conduit for an LFT device.

FIG. 4 shows another example of an arrangement of liquid conduits 40 for an LFT device which reduces the amount of liquid sample required compared to known LFT devices, with materials and functionality similar to the examples described above with reference to FIGS. 2 and 3. All elements are mounted to a self-adhesive backing 47. The sample S is received at a combined sample/conjugate pad 41/42 and propagates in the direction of arrow F to a reaction membrane 44. This embodiment has no cover tape because the transparent backing 44a of the reaction membrane 44 allows visibility of the test line reagents 43 and 45 under that backing. Excess sample is absorbed by a waste pad 46. Test results are visible in the direction of arrow T. This embodiment further simplifies the construction shown in FIG. 3.

Figure 5:
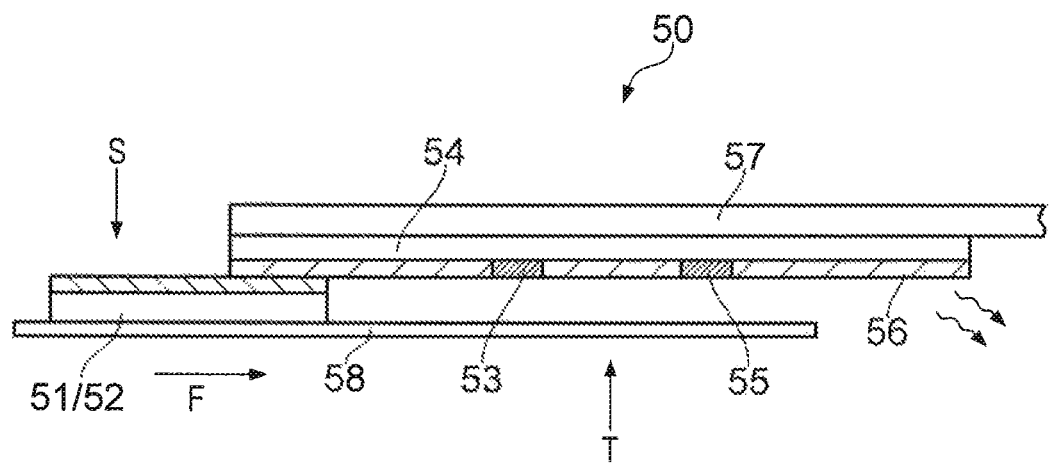
FIG. 5 shows a schematic view of a further liquid conduit for an LFT device.

FIG. 5 shows yet another example of an arrangement of liquid conduits 50 for an LFT device, which reduces the amount of liquid sample required compared to known LFT devices, with materials and functionality similar to the examples described above with reference to FIGS. 2 and 3. In this embodiment sample S is received on a combine sample receiving pad and conjugate storage pad 51/52, which includes a membrane as described above, for liquid transfer to a reaction pad 54. Test results are visible in the direction of arrow T. Rather than a waste wick pad, as described above, liquid is allowed to evaporate at an evaporation end 56, which is not covered by the cover strip 58. This embodiment further simplifies the construction of the LFT device shown in FIG. 4.

Figure 6:
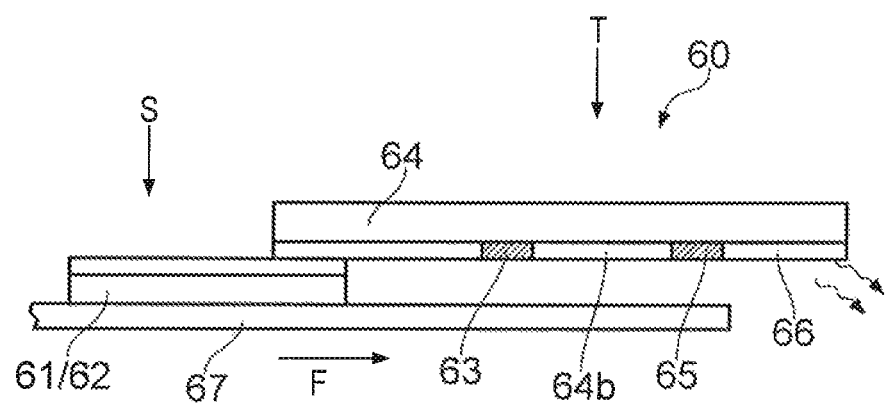
FIG. 6 shows a schematic view of a further liquid conduit for an LFT device.

FIG. 6 shows yet another example of an arrangement of liquid conduits 60 for an LFT device which reduces the amount of liquid sample required compared to known LFT devices, with materials and functionality similar to the examples described above FIGS. 2 and 3. Here a combined sample receiving and conjugate storage pad 61/62 is in fluid communication with a reaction pad 64, all mounted to a backing 67. Test results are visible in the direction of arrow T. Again the use of a waste wick is avoided by allowing evaporation form an uncovered portion 66 of the reaction pad membrane 64b. This embodiment further simplifies the construction shown in FIG. 5.

Figure 7:
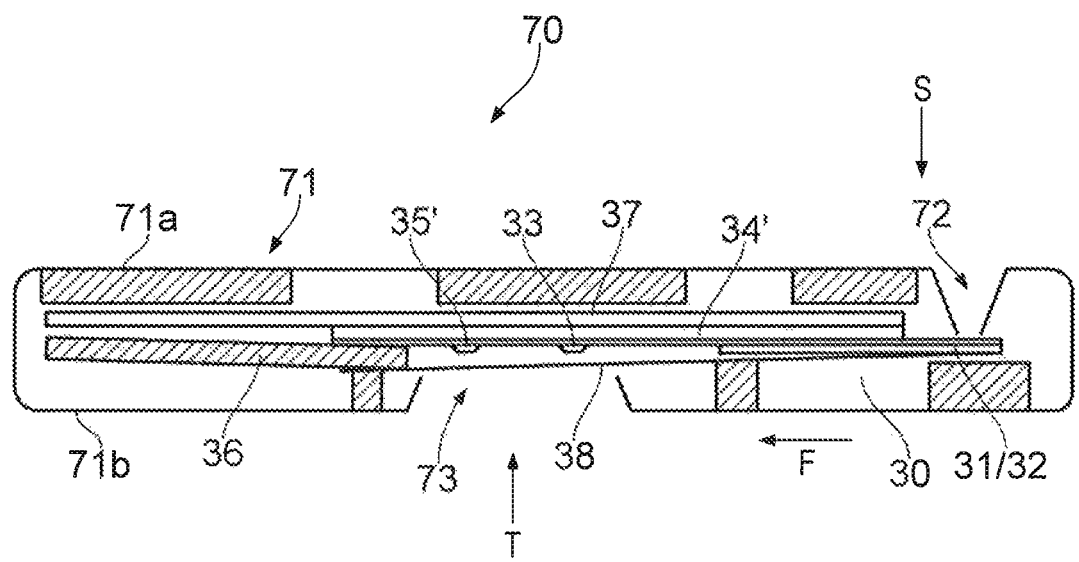
FIG. 7 shows an LFT device.

FIG. 7 shows an example of a LFT device 70 including a supporting housing 71 including a complementary upper housing 71a and lower housing 71b. The liquid conduit 30 used is as described with reference to FIG. 3. Sample liquid is supplied in the direction of arrow S at a housing recess 72 and propagates in the direction of arrow F along the conduit 30. Test lines 33 and 35 are visible through a window 73 in the housing, which is closed by the cover tape 38.

Figure 8:
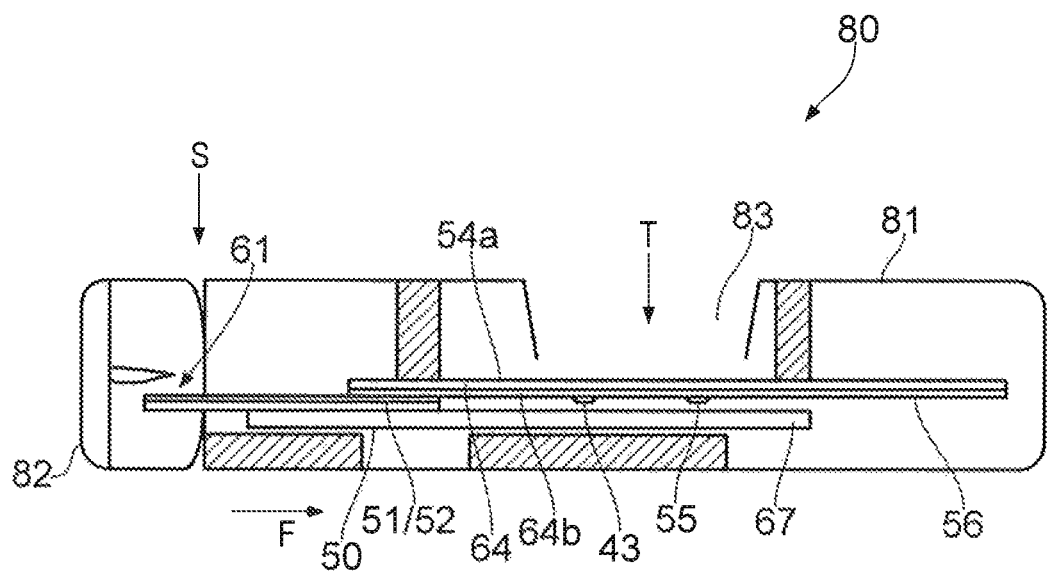
FIG. 8 shows a further LFT device.

FIG. 8 shows another LFT device 80, including a housing 81, with a removable finger prick cap 82, operable to provide a drop of blood. The device includes a liquid conduit 60 as described above with reference to FIG. 6. In use a sample, for example a blood drop obtained from the finger prick cap 82, is applied to a sample receiving area 61 of the conduit 60. Liquid phase of the sample propagates in the direction of arrow F. Test results are visible through a window 83 in the housing 81, which is closed by the transparent back 64a of the reaction membrane 64.

In the embodiments described above with reference to FIGS. 2 to 6, it will be observed that the sample receiving pads (with or without a combined conjugate storage pad) are formed from a substrate which is 50 µm thick CA material which has been cast by conventional means onto a transparent PET backing of about 100 µm thickness. The CA could be made thinner (for example 30 µm), but for mechanical strength and ease of handling, 50 µm is considered to be about right. CA of this thickness and of a pore size around 1.2 µm was found to have low inherent protein binding tendencies. RC materials of the same thickness and having the same backing have been found to work well also and have broadly the same properties, although RC has slightly lower protein binding tendencies. In particular both CA and RC make good receiving pads for blood, because their structure provides ready blood separation and recovery of plasma. It was found that colloidal gold of 40 nm particle size (used to bind to an analyte and show as a colour change at a capture test line) can easily migrate through CA and RC. Further, pore sizes down to 0.5 µm are considered to be satisfactory for use with colloidal gold particles. However, it was found that latex beads cannot readily migrate through these materials with pore sizes around 1 to 1.2 µm, and so if latex beads are used the pore sizes will need to be larger, for example above 1.4 µm. More particularly pore sizes around 2-3 µm are recommended if latex beads are used.

In experiments the lowest workable sample volume was found to be 10 µl for conventional 5 mm wide conduit strips, which resulted in significant reagent saving, and the constructions devised reduced the complexity of previous LFT devices also.

It will be observed also that the reaction pads described above are NC membrane material of about 50 µm in thickness having a backing layer of PET of about 100 µm in thickness. NC membranes have been found to have a low flow coefficient making them suitable for this application.

The use of a conventional waste wick has been described, which promotes sample propagation past the test lines. However, these may be omitted in the arrangements illustrated. It is the volume of sample propagating past the test lines that is important, and with the thin membranes described above, a lower volume than is normal provides satisfactory results. It has been found that only the first 10 µm of material depth can be viewed at the test lines, so any thicker material at the test line does not contribute significantly to the colour change definition at the test line. It follows that the thin membranes employed in this invention are sufficient to see the test line, and so the sample volume can be proportionally less without detracting from the efficiency of the test.

It will be appreciated that the drawings are prepared to schematically illustrate the principles of the invention and so the drawings are not to scale when the relative thicknesses described above are taken into account. Furthermore, in the drawings, for eases of reference, gaps are shown between elements. However, in practice the various elements shown will bend so that they lie one directly on top of another because they are thin.

Although certain embodiments have been described and illustrated, it will be apparent to the skilled addressee that additions, omissions and modifications are possible to those embodiments without departing from the scope of the invention claimed.

The invention claimed is:

1. A lateral flow test device comprising a backing material, and a liquid conduit element secured to the backing material, the liquid conduit element being formed from at least (i) a first, receiving, substrate, (ii) a second, conjugate, substrate, and (iii) a third, reaction, substrate, each of the first substrate the second substrate, and the third substrate having at least two layers, including:
   a) a substantially flat first layer of between 30 to 70 µm in thickness formed from a liquid porous material forming a liquid conduit; and
   b) a second layer of additional thickness formed from a generally non-porous polymer material and forming a backing to the first layer, the second layer being positioned adjacent to the first layer;
wherein the first layer of the first substrate is a regenerated cellulose (RC) membrane having little or no protein binding capacity or is a cellulose acetate (CA) membrane having a low protein binding capacity, wherein the first layer of the second substrate is formed from a nitrocellulose having a high protein binding capacity of at least 3 µg/cm$^2$, and wherein the first substrate the second substrate, and the third substrate overlap in series such that their respective first layers are in contact where the respective substrates overlap.

2. The lateral flow test device of claim 1, wherein each first layer has an average pore size of 0.5 to 3 μm.

3. The lateral flow test device of claim 1, wherein each second layer is transparent and is formed from a plastics material including a polyester.

4. The lateral flow test device of claim 1, wherein each second layer is about 100 μm in thickness.

5. The lateral flow test device of claim 1, comprising a plurality of liquid conduit elements secured to the backing material, wherein the plurality of liquid conduit elements comprises the liquid conduit element.

6. The lateral flow test device of claim 1, wherein the first substrate of the liquid conduit element includes an element for receiving a sample.

7. The lateral flow test device of claim 1, wherein the second substrate of the liquid conduit element includes an element for conjugate storage.

8. The lateral flow test device of claim 6, wherein the element for receiving the sample includes a portion which provides conjugate storage.

9. The lateral flow test device of claim 1, wherein the third substrate of the liquid conduit element includes a reaction element including one or more reagents for reacting with a bound analyte.

10. The lateral flow test device of claim 9, wherein the reaction element is formed from a layered material including a first layer formed from nitrocellulose membrane and a second layer formed from a polymer.

11. The lateral flow test device of claim 10, wherein the first layer of the layered material is about 40 to 60 μm in thickness, and wherein the second layer of the layered material is about 100 μm in thickness.

12. The lateral flow test device of claim 11, wherein the reaction element includes an uncovered portion for allowing sample liquid evaporation.

13. The lateral flow test device of claim 12, wherein overlapping portions of the respective first layers of the first substrate and the second substrate are in fluid communication with one another.

14. A lateral flow test device comprising a backing material, and a liquid conduit element secured to the backing material, the liquid conduit element being formed from at least (i) a first, receiving, substrate, (ii) a second substrate, and (iii) a third substrate, each of the first substrate the second substrate, and the third substrate having at least two layers, including:
   a) a substantially flat first layer not exceeding 75 μm in thickness formed from a liquid porous material forming a liquid conduit; and
   b) a second layer of additional thickness formed from a generally non-porous polymer material and forming a backing to the first layer, the second layer being positioned adjacent to the first layer;
   wherein the first layer of the first substrate has no, or has a low protein binding capacity, wherein the first layer of the second substrate has a high protein binding capacity of at least 3 μg/cm$^2$, and wherein the first substrate the second substrate, and the third substrate overlap in series such that their respective first layers are in contact where the respective substrates overlap.

15. The lateral flow test device of claim 14, wherein the thickness of the first layer is between 30 to 70 μm.

16. The lateral flow test device of claim 14, wherein each first layer has an average pore size of 0.5 to 3 μm.

17. The lateral flow test device of claim 14, comprising a plurality of liquid conduit elements secured to the backing material, wherein the plurality of liquid conduit elements comprise the liquid conduit element.

* * * * *